US006162206A

United States Patent [19]

Bindokas et al.

[11] Patent Number: 6,162,206
[45] Date of Patent: *Dec. 19, 2000

[54] RESEALABLE ACCESS SITE

[75] Inventors: Algirdas J. Bindokas, Clarendon Hills; Birendra K. Lal, Lake Zurich; Ray Brausam, Antioch; Thomas A. Stonis, Crystal Lake; Steven C. Jepson, Palatine; Michael W. Scharf, McHenry; David V. Bacehowski, Wildwood; Michael T. K. Ling, Vernon Hills, all of Ill.; Hugh M. Forman, Brookfield, Wis.; Daniel J. Rudolph, Chicago, Ill.

[73] Assignee: Baxter International Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/996,642

[22] Filed: Dec. 23, 1997

[51] Int. Cl.[7] .................... A61M 39/00

[52] U.S. Cl. .................... 604/533; 604/534; 604/905

[58] Field of Search .................... 604/167, 169, 604/170, 256, 283, 414, 415, 416, 905, 533, 534, 535, 536, 539; 251/149.1

[56] References Cited

U.S. PATENT DOCUMENTS

| | | |
|---|---|---|
| 1,180,655 | 4/1916 | McElroy . |
| 2,436,291 | 2/1948 | Daniel . |
| 2,546,672 | 3/1951 | LeClair . |
| 2,579,724 | 12/1951 | Breakstone . |
| 2,989,053 | 6/1961 | Hamilton . |
| 2,998,635 | 9/1961 | Burritt, Jr. et al. . |
| 3,057,350 | 10/1962 | Cowley . |
| 3,171,412 | 3/1965 | Braun . |
| 3,313,299 | 4/1967 | Spademan . |
| 3,332,418 | 7/1967 | Brody . |
| 3,376,866 | 4/1968 | Ogle . |
| 3,729,031 | 4/1973 | Baldwin . |
| 3,729,032 | 4/1973 | Tischlinger et al. . |

(List continued on next page.)

FOREIGN PATENT DOCUMENTS

| | | |
|---|---|---|
| 2124970 | 12/1994 | Canada . |
| 0111723 | 8/1983 | European Pat. Off. . |
| WO 84/04063 | 10/1984 | WIPO . |
| 9508974 | 4/1995 | WIPO . |
| WO 95/15195 | 6/1995 | WIPO . |
| WO 96/22681 | 9/1996 | WIPO . |

*Primary Examiner*—John G. Weiss
*Assistant Examiner*—David J. Cho
*Attorney, Agent, or Firm*—Jeffrey C. Nichols; Mark J. Buonaiuto; Francis C. Kowalik

[57] ABSTRACT

A resealable access site (10) is provided for allowing a cannula (18) multiple accesses to an internal cavity (35) defined by a container (12). The access site (10) includes a first conduit (28) defining a passageway (29) forming a fluid path to the cavity within the container. Sealingly attached to the conduit (28) is a housing (26) with a lower portion (**26*a*) and a lower flange (68) attached to a lower end of the lower portion and extending radially inward from the lower portion. A septum (24) is disposed and compressed within the lower portion, with the septum defining an opening (46) extending upward through at least a portion of the septum. The opening (46) is sized for insertion of the cannula (18) through the septum (24) with the septum sealing about the exterior of the cannula. The septum (24) is maintained in the housing by the support provided by the opposing flange (68) and conduit (28**).

21 Claims, 3 Drawing Sheets

U.S. PATENT DOCUMENTS

| | | | |
|---|---|---|---|
| 3,776,229 | 12/1973 | McPhee . | |
| 3,853,127 | 12/1974 | Spademan . | |
| 3,976,073 | 8/1976 | Quick et al. . | |
| 3,977,400 | 8/1976 | Moorehead . | |
| 3,986,508 | 10/1976 | Barrington . | |
| 3,990,445 | 11/1976 | Lundquist . | |
| 3,995,630 | 12/1976 | van de Veerdonk . | |
| 4,000,739 | 1/1977 | Stevens . | |
| 4,000,740 | 1/1977 | Mittleman . | |
| 4,048,995 | 9/1977 | Mittleman . | |
| 4,048,996 | 9/1977 | Mittleman et al. . | |
| 4,133,441 | 1/1979 | Mittleman et al. . | |
| 4,134,512 | 1/1979 | Nugent . | |
| 4,143,853 | 3/1979 | Abramson . | |
| 4,166,467 | 9/1979 | Abramson . | |
| 4,197,848 | 4/1980 | Garrett et al. . | |
| 4,219,912 | 9/1980 | Adams . | |
| 4,236,880 | 12/1980 | Archibald . | |
| 4,243,034 | 1/1981 | Brandt . | |
| 4,259,276 | 3/1981 | Rawlings . | |
| 4,277,226 | 7/1981 | Archibald . | |
| 4,289,129 | 9/1981 | Turner . | |
| 4,294,249 | 10/1981 | Sheehan et al. . | |
| 4,303,067 | 12/1981 | Connolly et al. . | |
| 4,322,201 | 3/1982 | Archibald . | |
| 4,334,551 | 6/1982 | Pfister . | |
| 4,387,879 | 6/1983 | Tauschinski . | |
| 4,405,316 | 9/1983 | Mittleman . | |
| 4,411,662 | 10/1983 | Pearson . | |
| 4,412,573 | 11/1983 | Zdeb . | |
| 4,416,661 | 11/1983 | Norman et al. . | |
| 4,424,833 | 1/1984 | Spector et al. . | |
| 4,434,822 | 3/1984 | Bellamy et al. . | |
| 4,443,219 | 4/1984 | Meisch et al. . | |
| 4,449,693 | 5/1984 | Gereg . | |
| 4,475,548 | 10/1984 | Muto . | |
| 4,496,348 | 1/1985 | Genese et al. . | |
| 4,511,359 | 4/1985 | Vaillancourt . | |
| 4,578,063 | 3/1986 | Inman et al. . | |
| 4,610,469 | 9/1986 | Wolff-Mooij . | |
| 4,610,665 | 9/1986 | Matsumoto et al. . | |
| 4,610,674 | 9/1986 | Suzuki et al. . | |
| 4,626,245 | 12/1986 | Weinstein . | |
| 4,634,424 | 1/1987 | O'Boyle . | |
| 4,637,817 | 1/1987 | Archibald et al. . | |
| 4,653,539 | 3/1987 | Bell . | |
| 4,673,390 | 6/1987 | Archibald . | |
| 4,673,393 | 6/1987 | Suzuki et al. . | |
| 4,675,020 | 6/1987 | McPhee . | |
| 4,703,759 | 11/1987 | Merrick et al. . | |
| 4,705,506 | 11/1987 | Archibald . | |
| 4,712,583 | 12/1987 | Pelmulder et al. . | |
| 4,714,463 | 12/1987 | Archibald et al. . | |
| 4,723,550 | 2/1988 | Bales et al. . | |
| 4,735,311 | 4/1988 | Lowe et al. . | |
| 4,752,287 | 6/1988 | Kurtz et al. . | |
| 4,752,292 | 6/1988 | Lopez et al. . | |
| 4,758,225 | 7/1988 | Cox et al. . | |
| 4,768,568 | 9/1988 | Fournier et al. . | |
| 4,776,843 | 10/1988 | Martinez et al. . | |
| 4,781,680 | 11/1988 | Redmond et al. . | |
| 4,781,693 | 11/1988 | Martinez et al. . | |
| 4,781,702 | 11/1988 | Herrli . | |
| 4,798,594 | 1/1989 | Hillstead . | |
| 4,804,366 | 2/1989 | Zdeb et al. . | |
| 4,809,679 | 3/1989 | Shimonaka et al. . | |
| 4,857,062 | 8/1989 | Russell . | |
| 4,874,369 | 10/1989 | Kalle et al. . | |
| 4,874,377 | 10/1989 | Newgard et al. . | |
| 4,874,378 | 10/1989 | Hillstead . | |
| 4,886,495 | 12/1989 | Reynolds . | |
| 4,889,256 | 12/1989 | Fowles . | |
| 4,889,527 | 12/1989 | Herrli . | |
| 4,892,222 | 1/1990 | Schmidt et al. . | |
| 4,895,346 | 1/1990 | Steigerwald . | |
| 4,932,409 | 6/1990 | Hirschberg . | |
| 4,932,633 | 6/1990 | Johnson et al. . | |
| 4,935,010 | 6/1990 | Cox et al. . | |
| 4,950,260 | 8/1990 | Bonaldo . | |
| 4,960,412 | 10/1990 | Fink . | |
| 5,009,391 | 4/1991 | Steigerwald . | |
| 5,017,192 | 5/1991 | Dodge et al. . | |
| 5,071,404 | 12/1991 | Larkin et al. . | |
| 5,071,413 | 12/1991 | Utterberg . | |
| 5,078,948 | 1/1992 | Troutman et al. . | |
| 5,080,654 | 1/1992 | Picha et al. . | |
| 5,085,645 | 2/1992 | Purdy et al. . | |
| 5,088,984 | 2/1992 | Fields . | |
| 5,088,995 | 2/1992 | Packard et al. . | |
| 5,098,385 | 3/1992 | Walsh . | |
| 5,098,393 | 3/1992 | Amplatz et al. . | |
| 5,100,394 | 3/1992 | Dudar et al. . | |
| 5,108,702 | 4/1992 | Hubner | 604/415 |
| 5,113,911 | 5/1992 | Hirsh . | |
| 5,114,408 | 5/1992 | Fleischhaker et al. | 604/167 |
| 5,116,021 | 5/1992 | Faust et al. . | |
| 5,135,489 | 8/1992 | Jepson et al. . | |
| 5,141,498 | 8/1992 | Christian . | |
| 5,149,327 | 9/1992 | Oshiyama . | |
| 5,158,546 | 10/1992 | Haber et al. | 604/87 |
| 5,158,554 | 10/1992 | Jepson et al. . | |
| 5,167,238 | 12/1992 | Newman . | |
| 5,167,648 | 12/1992 | Jepson et al. . | |
| 5,171,234 | 12/1992 | Jepson et al. . | |
| 5,178,107 | 1/1993 | Morel, Jr. et al. . | |
| 5,178,607 | 1/1993 | Lynn et al. . | |
| 5,188,620 | 2/1993 | Jepson et al. | 604/283 |
| 5,199,947 | 4/1993 | Lopez et al. . | |
| 5,199,948 | 4/1993 | McPhee . | |
| 5,201,717 | 4/1993 | Wyatt et al. . | |
| 5,201,725 | 4/1993 | Kling . | |
| 5,203,775 | 4/1993 | Frank et al. . | |
| 5,211,634 | 5/1993 | Vaillancourt . | |
| 5,211,638 | 5/1993 | Dudar et al. . | |
| 5,215,537 | 6/1993 | Lynn et al. . | |
| 5,242,393 | 9/1993 | Brimhall et al. . | |
| 5,242,423 | 9/1993 | Goodsir et al. . | |
| 5,251,873 | 10/1993 | Atkinson et al. . | |
| 5,254,097 | 10/1993 | Schock et al. . | |
| 5,279,571 | 1/1994 | Larkin . | |
| 5,290,241 | 3/1994 | Kraus et al. . | |
| 5,295,657 | 3/1994 | Atkinson | 251/149.1 |
| 5,295,658 | 3/1994 | Atkinson et al. . | |
| 5,300,034 | 4/1994 | Behnke et al. . | |
| 5,340,359 | 8/1994 | Segura Badia | 604/283 |
| 5,389,086 | 2/1995 | Attermeier et al. | 604/905 |
| 5,393,101 | 2/1995 | Matkovich | 604/905 |
| 5,400,500 | 3/1995 | Behnke et al. . | |
| 5,401,245 | 3/1995 | Haining . | |
| 5,403,293 | 4/1995 | Grabenkort . | |
| 5,403,525 | 4/1995 | Helgren et al. . | |
| 5,405,331 | 4/1995 | Behnke et al. . | |
| 5,405,340 | 4/1995 | Fageol et al. . | |
| 5,429,619 | 7/1995 | Furnish | 604/283 |
| 5,437,650 | 8/1995 | Larkiin et al. | 604/283 |
| 5,573,516 | 11/1996 | Tyner . | |
| 5,899,888 | 5/1999 | Jepson et al. . | |

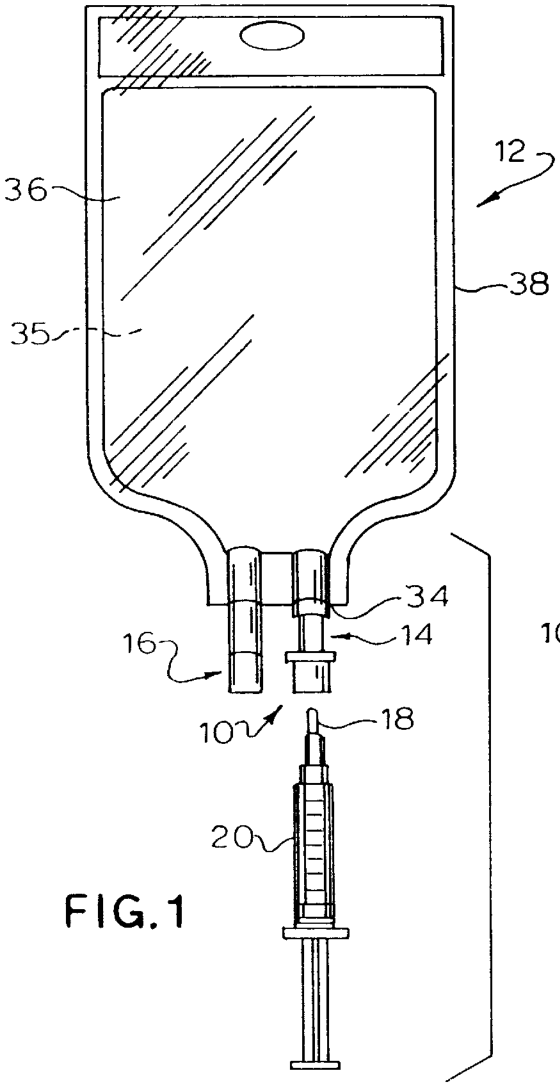
FIG. 1
FIG. 2
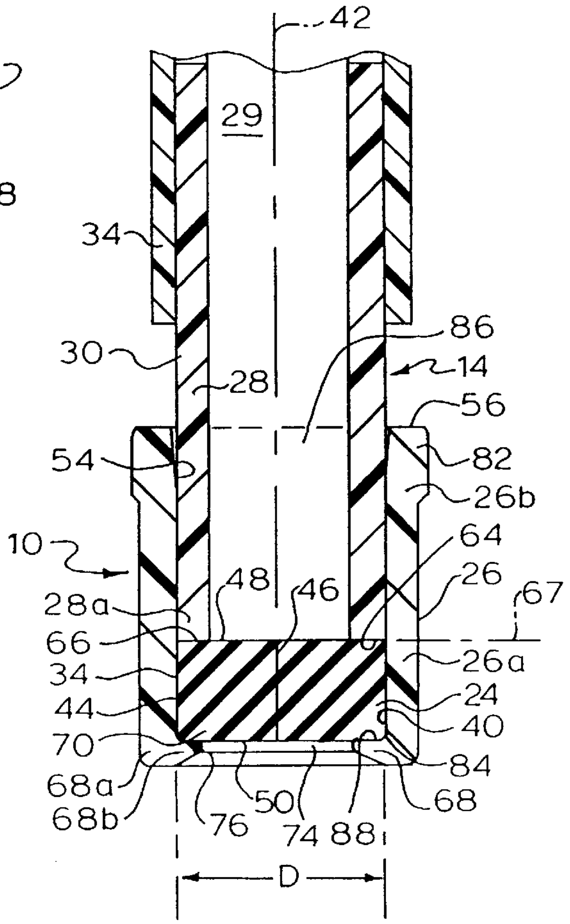
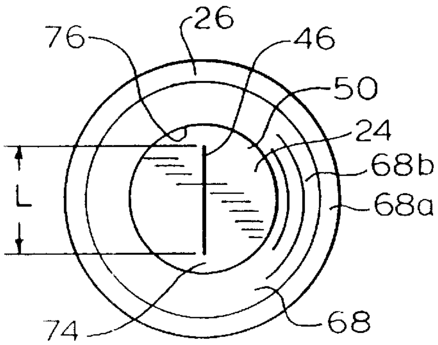
FIG. 2A
FIG. 3
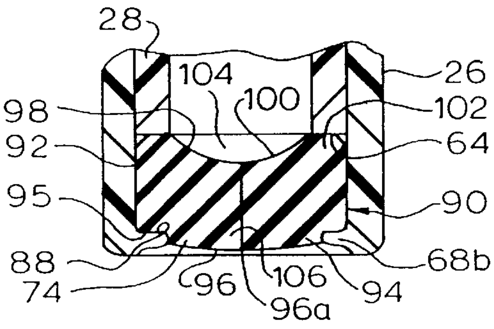

RESEALABLE ACCESS SITE

FIELD OF THE INVENTION

The present invention generally relates to a resealable access site for a fluid conveying conduit and more particularly relates to a resealable fluid access port for a fluid filled container such as a container containing fluid such as blood, medication or nutritional fluids which is to be provided to a patient.

BACKGROUND OF THE INVENTION

Frequently fluids are provided to a patient by establishing a connection between the patient and a container housing the fluids. For example, medication may be provided by establishing a connection between the venous system of the patient and a container housing the medication. The medication may be supplied singularly or in solution with another fluid such as a saline or dextrose solution. The connection between the container and patient is typically established with an intravenous ("I.V.") administration "set." One method of providing the needed medication is to place the medication in an I.V. solution container before the container is supplied to a health care provider. Additional methods may include providing a portion of the solution to the provider, and injecting a supplemental medication into the container just before or during administration of the container contents to the patient.

Nutrition may also be provided to a patient by establishing a connection between a container containing nutritional fluid and a patient. The connection may be to a patient's venous or digestive system. During the "feeding" of a patient, supplemental fluids may need to be added to the container.

The medical solution or nutritional containers are typically formed with at least one port which provides or defines a passageway to the fluid contained within the container. To prevent leakage of fluid through the port, the container must include some manner or means for sealing the port. Should the function of the port be such that it is intended for a single insertion of a piercing member, forming a part of the administration set, to establish a fluid connection between the container and the set, the sealing member may take the form of a membrane stretched across the passageway. The piercing member may be referred to as a "spike". These types of ports are typically referred to as administration or "admin" ports.

It is also frequently necessary to establish intermittent access to the container fluid for the removal or addition of fluids such as medication or nutritional supplements to the container contents. The intermittent addition/removal port is sometimes referred to as the "med" port or site. In this instance, the site typically has a resealable access assembly which may be pierced by an access device, and then upon removal of the access device, the assembly reseals to prevent leakage from the container. This assembly includes a resealable member which may take the form of a solid rubber body, which must be pierced by a sharp cannula, such as a needle. The needle typically forms part of a syringe. However, use of a needle poses a danger of accidental "needle stick".

The resealable member may also take the form of a pre-slit septum which is adapted to be penetrated by a blunt cannula although use of the sharpened cannula is also acceptable. The blunt cannula is particularly adapted to overcome the potential danger of needle stick. Such septums and blunt cannulas are described in U.S. Pat. No. 5,135,489 is incorporated by reference herein.

These fluid filled containers may take many forms. One of the more prevalent forms is where the container is constructed as a flexible bag, which is suspended generally above the point of entry or access site into the patient. The bag container may be supplied with a single port or with a plurality of ports with one of the plurality being the administration port and another of the ports being the med port.

One method of fabricating the container is to place the fluid in the container during fabrication and then the assembled, fluid-filled container is subjected to a sterilization process. The preferred method of sterilization typically involves autoclaving or exposing the container to steam so that the container and its contents are subjected to a high temperature for an extended period of time. It has been found that this high temperature exposure may negatively impact on the performance characteristics of the components of known resealable access sites.

Also, generally the resealable septum is disposed within a housing particularly configured to position and compress the septum to maintain the resealable properties. It has also been found that these housings add an appreciable cost to a resealable access site and thus the cost of the container. As a large number of these containers are used by health care providers, any incremental cost has a large negative impact on the cost incurred in providing health care to a patient.

In addition to being employed on ports for fluid filled containers resealable septums are also employed in other devices such as injection sites, connector devices and blood sampling devices or the like. Providing particularly configured housings and resealable septums may add an appreciable cost to the manufacturing of these devices.

Therefore, it is an object of the present invention to provide a resealable access site for a fluid conveying conduit.

It is another object of the present invention to provide an improved resealable access site for a fluid-filled container, and more particularly, to provide an improved fluid access site for a container containing fluid which is to be administered to a patient.

It is a further object of the present invention to provide an improved resealable access site which may be pierced by an access device adapted to reduce the danger of accidental needle stick.

It is yet another object of the present invention to provide an improved access site for a fluid filled container in which the container and site may be exposed to high temperatures such as the temperatures present in a steam sterilization process.

It is yet another object of the present invention to provide an improved access site which may be economically fabricated. A related object is to provide such an access site which may be combined with a container containing fluid which is to be administered internally to a patient such as intravenously or parenterally.

SUMMARY OF THE INVENTION

Accordingly a resealable access site for allowing a cannula, including a blunt or sharpened cannula, multiple accesses to a fluid conveying passageway is provided. The access site includes a conduit defining the passageway. A lower end of the conduit forms a lower ring shaped land area. Sealingly attached to the conduit is a housing with a lower portion having an upward extending inner surface and a lower flange attached to a lower end of the lower portion and extending radially inward from the lower portion. The housing also includes an upper portion with the conduit attached to the upper portion.

A generally disk shaped septum is disposed and radially compressed within the lower portion, with the septum defining an opening extending upward through at least a portion of the septum. The opening is sized for insertion of the cannula through the septum with the septum sealing about the exterior of the cannula. The septum is compressed to seal the opening before and after insertion of the cannula. The septum may also be formed with the upper and lower surface having other configurations to accent particular attributes which are desirable for a specific application.

To maintain the septum properly positioned within the housing, the land area of the conduit is in close proximity to the upper edge portion and the radial flange extends over the lower edge portion. An inner edge of the radial flange defines a target or access area or opening to the septum.

In a preferred embodiment, the conduit includes first tube which provides a passageway to an internal cavity defined by a fluid filled container. A lower end of the first tube forms the lower ring shaped land area. Also in the preferred embodiment, the housing is provided as a unitary housing with the lower flange integrally attached to a lower end of the lower portion and extending radially inward from the lower portion.

An inner surface of the lower portion of the housing is cylindrically shaped, and an inner surface of the upper portion is frustroconical shaped with a wider upper end. The taper facilitates the insertion and compressing of the septum within the housing during assembly of the access site. The first tube is then inserted and the lower land area is preferably formed with a flat extending surface to contact and engage the septum with the septum entirely disposed within the lower portion of the housing.

An alternate embodiment of the septum is provided. The septum includes a lower domed portion which extends at least partially through the access opening. An upper surface of the septum may be formed with a concave depression to accommodate material displaced upon insertion of the cannula.

A further alternate embodiment of the septum is provided, whereby the septum includes a lower portion attached to an upper barrier layer. The upper layer prevents contact between fluid in the cavity of the container and the lower portion thereby expanding the number of satisfactory materials the lower portion may be fabricated from.

Further alternate embodiments of the resealable access site for allowing a cannula, including a blunt or sharpened cannula, multiple accesses to a fluid conveying passageway are provided. Each of these embodiments include particular features which facilitate use of the site in various applications. In general, these alternate embodiments are particularly suited for use with fluid filled containers although other applications are also contemplated.

BRIEF DESCRIPTION OF THE DRAWINGS

FIG. 1 is a front elevational view of a preferred embodiment of a resealable access site of the present invention, shown as forming a part of an intravenous solution container;

FIG. 2 is a side sectional view of the access site of FIG. 1;

FIG. 2*a* is a bottom planar view of the access site of FIG. 1;

FIG. 3 is an alternate embodiment of the resealable septum forming a part of the access site of FIG. 1;

DESCRIPTION OF THE PREFERRED EMBODIMENT

Figure 4:
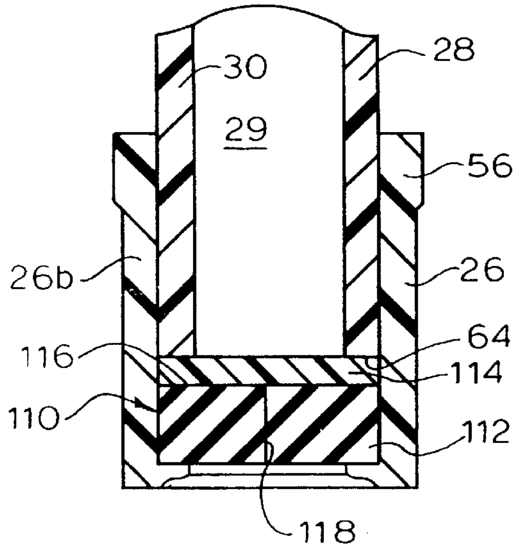
FIG. 4 is a further alternate embodiment of the resealable septum forming a part of the access site of FIG. 1.

A detailed description of preferred and alternate embodiments of the present invention is now provided with specific reference being made to the drawings in which corresponding features among the various Figures are designated with identical reference numerals.

Referring to FIG. 1, a preferred embodiment of a resealable access site is generally indicated at 10 and is shown as forming a part of a flexible intravenous (IV) solution container, indicated generally at 12. The access site 10 may also form a part of other devices including injection sites, blood sampling devices, cannulas and the like.

The shown container is an intravenous solution container composed of flexible film. The film may be constructed of materials containing polyvinylchloride (PVC). In addition, the container 12 may take other forms and be composed of other film materials such as the films shown and described in U.S. patent application entitled Polymeric Compositions for Medical Packaging and Devices, Ser. No. 08/153,823, Filed Nov. 16, 1993, and U.S. patent application entitled Multilayered Polymeric Based Film Structure for Medical Grade Products, Ser. No. 08/153,602, filed Nov. 16, 1993, both of which are assigned to the assignee of the present invention and are incorporated by reference herein.

The access site 10 is formed as a part of an access port 14 of the container 12. The container 12 may include a single access port or a plurality of access ports. In addition, the container 12 may also include ports having other configurations such as the container shown in FIG. 1 which also includes an administrative port 16 particularly suited as a single access site for the container 12. One embodiment of the container 12 being a VIAFLEX® solution bag manufactured by Baxter International Inc. of Deerfield, Ill.

The access site 10 is particularly suited for multiple access by a cannula 18, preferably a blunt cannula. Sharpened cannula are also acceptable; however, use of such cannula may present a health hazard. Typically the cannula forms a part of a syringe 20, for example to inject or withdraw fluids from the container. The cannula 18 may include an INTERLINK® cannula sold by Becton-Dickinson, Inc. of Morristown, N.J.

Referring also to FIG. 2, the site 10 includes a compressible resilient septum 24 which is compressingly disposed within a housing 26. The housing 26 is in turn attached about a lower end 28*a* of a conduit 28 which is preferably shaped in a cylindrical configuration. The conduit 28 defines a passageway 29 for fluid flow and may be formed as a part of various medical devices and be composed of one layer or a multiple of layers. When the access site 10 forms a part of the access port 14, the conduit 28 is preferably formed from a plurality of elements including a flexible intermediate tube 30 which is sealingly attached to a generally cylindrical port tube 34. The conduit 28 may also include just the port tube 34 without use of the intermediate tube 30.

The intermediate tube 30 may be composed of PVC or other materials which are suitable for the application such as PCCE 9966, manufactured by Eastman Chemical Products, Inc.; HYTREL 4056 thermoplatic polyester elastomer manufactured by DuPont Engineering Polymers; PL 795, manufactured by Baxter Healthcare, Inc. or the like, which do not contain PVC.

The port tube 34 provides access to a fluid containing cavity 35 formed by similarly configured, juxtaposed sidewalls 36 which are sealingly attached to each other about their peripheral edges. The sidewalls 36 are generally flexible and form a bag 38 to contain the fluid. The port tube 14 extends through and is bonded to the sidewalls 36 to provide environmentally sealed access to the cavity 35.

Referring to FIG. 2 in particular, the septum 24 is preferably entirely disposed within the lower end 26*a*. An axially extending interior surface 40 of the lower end 26*a* of the housing 26 contacts a circumferential sidewall 44 of the septum 24 and compresses the septum in an inward radial direction toward a central axis 42 which is defined by the interior surface 40 of the lower end 26*a* of the housing 26. The interior surface 40 also is preferably formed with a smooth surface free of protrusions, etc.

The interior surface 40 is cylindrically shaped, with a constant radius about the axis 42 so that the radial compression of the septum 24 within the housing 26 does not cause the septum to creep in an upward direction during assembly or use of the site 10. The compression exerted on the septum 24 by the internal surface 40 causes the sidewall 44 of the septum to deform into a similarly configured cylindrical configuration, although it is preferred that the septum 24 is fabricated to have generally cylindrical sidewalls 44 in an uncompressed state.

Referring in particular to FIG. 2*a*, the septum 24 has a resealable opening 46 forming a slit when the septum is disposed in the housing 26. The opening 46 extends upward through at least a portion of the septum 24 and preferably the entire thickness of the septum, i.e., extending from a top surface 48 (FIG. 2) to a bottom surface 50 of the septum.

The opening 46 defines a length L which is preselected to allow for sliding penetration and extension of the cannula 18 (FIG. 1) through the septum 24. As the cannula 18 penetrates the septum 24, the opening 46 deforms into a shape which conforms about the circumferential surface of the cannula. The length L is preferably less than half the circumferential distance about the surface of the cannula so that the opening 46 is stretched during penetration of the septum 24 by the cannula. Upon stretching, the elasticity of the septum 24 causes a compressive radial force to be applied by the septum on the cannula 18 to seal about the cannula and prevent leakage of the contents of the container 12 along the interface between the cannula and septum.

Referring also to FIG. 2, to seal the opening 46 before insertion and after removal of the cannula 18 (FIG. 1), the septum 24 and housing 26 are sized so that during assembly of the site assembly 14, insertion of the septum into the housing causes the housing to apply an inwardly directed radial compressive force on the septum. As can be appreciated, this compressive force is maintained by compressively fitting the septum 24 into the lower end 26*a* of the housing 26. This compressive fit comes about by manufacturing the septum 24 with a diameter which is greater than the diameter D of the internal surface 40 of the lower end 26*a*. The amount of compression which is desired should be sufficient to seal the slit 46 to prevent leakage of the fluid in the container 12 before, during and after insertion of the cannula 18 (FIG. 1).

In flexible containers 12, the pressure of the fluid will typically be generated by the head pressure of the fluid. It can also be appreciated that the container may also be pressurized so that additional pressure is exerted by the fluid on the opening 46. Therefore, the compressive force needed for sealing the opening 46 may vary depending on the application. However, the greater the compressive force exerted on the opening 46 by the compressive fit, generally the higher the insertion force needed to penetrate the septum 24 with the cannula 18.

For example, in a port for an intravenous solution bag, it has been found that the % compression of the septum 24, i.e., the difference in the diameter of the septum before and after compression within the housing divided by the original diameter of the septum, should range between 2% and 15%. An approximate 11% compression has been found to be sufficient for most of such applications. The % compression also relates to the compression after assembly and any sterilization procedures.

To facilitate the insertion of the septum 24 into the lower end 26*a* of the housing 26 during assembly, an interior sidewall surface 54 of an upper portion 26*b* of the housing is formed in a frustoconical shape with a wider upper end.

The septum 24 is also preferably fabricated so that in the uncompressed state the top surface 48 and bottom surface 50 are generally flat. When the septum 24 is then compressed in the housing 26, the top surface 48 and bottom surface 50 may form a slight bulge.

The conduit 28 is also sized so insertion of the lower end 28*a* into the housing 26 causes the housing to exert a radial compressive force on the lower end. The compressive force between the conduit 28 and housing 26 facilitates the formation of a sealed attachment between the tube and housing. Typically, bonding agents such as adhesives and/or solvents such as cyclohexanone or the like are used to achieve the sealed attachment with the bonding agent selected to be compatible with the housing 26 and conduit 28. Also the bonding agent chosen and placement of the bonding agent should not give rise to potential contamination of the contents of the container 12.

The conduit 28 provides support for the septum 24 so that the septum is not displaced into the passageway during insertion of the cannula 18 (FIG. 1). When the conduit 28 is a part typically found in a device such as the intermediate tube 30 of a container 12, the access site 10 may be provided at a lower cost.

To provide the septum support, the conduit 28 is configured to form a radially extending flat ring-shaped land area 64 which supportingly extends adjacently about an outer circumferential edge portion 66 of the upper surface 48 of the septum 24. In addition, in the preferred embodiment, the land area 64 is located proximate the edge portion 66 and preferably abuttingly contacts the edge portion with the septum entirely disposed below a plane 67 defined by the land area.

As noted above, in the preferred embodiment of the access port 14, the conduit 28 includes the intermediate tube 30 and the port tube 34 with the intermediate tube 30 forming the land area 64. Utilizing both an intermediate tube 30 and port tube 34 allows the port tube to be thinner than if it functioned as the support. Thus the port tube 34 may be constructed with thin walls and be very flexible, which is a desirable feature.

To provide a lower support to the septum 24, the housing 26 includes a lower radial flange portion 68 which is preferably integrally connected to the lower end 26*a* of the housing. The flange portion 68 extends inward over a circumferential edge portion 70 of the lower surface 50 of the septum 24 with the septum 24 preferably disposed entirely above the flange 68. The flange portion 68 is formed with a peripheral radially extending flat portion 68*a* and an inner portion 68*b* extending inward from the outer circumferential portion 68*a* and defining an opening or target area 74 for the insertion of the cannula 18. The inner portion 68*b* is tapered to a thinned inner edge 76.

The intermediate tube 30 is sealingly bonded to the port tube 34 by a suitable bonding agent such as an adhesive or solvent or the like. Preferably the intermediate tube 30 extends within the port tube 34. To facilitate economical manufacture of the access port 14, the access site 10 is preferably assembled separately from the bag 38, and then later, sealingly attached to the port tube 34 by the bonding agent.

Separate assembly of the port 14 also allows sterilization of the access site 14 using procedures which may not be suitable for the whole container 12. For example, after assembly, the access site 10 may be exposed to gamma radiation for sterilization purposes. Gamma radiation may have an effect on certain materials used to manufacture the bag portion 38. After sterilization, the access site 10 is attached to the bag 38 and forms a component of the assembled container 12.

After fabrication, the filled container 12 may undergo a sterilization process. In the typical sterilization process, the assembled container 12 is subjected to steam to elevate the temperature of the container and contents for an extended period of time. When elevated to this high temperature, the housing 26 of the resealable port 14 may have a tendency to relax due to the radially outward directed forces exerted by the compressed septum on the housing. Therefore in instances where steam sterilization is required, the housing 26 should be constructed so that the housing does not relax through relaxation or radial expansion to a point where there is insufficient % compression and compressive force exerted on the septum 24 to keep the opening 46 sealingly closed before and after removal of the cannula 18. In the preferred embodiment, the housing 26 is composed of polycarbonate which provides excellent resistance to relaxation during the sterilization process. Polysulfone is also satisfactory; however, polysulfone typically adds to the cost of the site assembly 14. In addition, other polymeric materials, such as polypropylene may perform satisfactorily; however, polypropylene has a tendency to relax when exposed to high temperatures to a much greater degree than polycarbonate or the like.

When composed of polycarbonate or the like, the housing 26 is formed using injection molding. Injection molding, however, may cause the creation of stress points in the housing 26 where the housing may crack during steam sterilization, or during use of the container 12 by the health care provider. For example, weld lines, which are formed when two separate cooling flows of injection molding material contact each other during the injection process, are typically high-stress points. Also, sharp edges are typically the site of high stress points. To prevent the formation of a weld line, the housing includes an upper thickened flange section 82 which, during injection molding, provides a larger pathway for the flow of the molten material within the corresponding portion of a mold (not shown) for the housing 26. Upon injection of the molten material, the material flows in two directions about the circumference of the mold and the flows contact each other before cooling substantially preventing the resulting formation of the weld line. The molten material then flows into the other portions of the mold to form the complete housing 26.

It is also envisioned that the housing 26 could be formed by extrusion molding using techniques employed in the manufacture of corrugated air supply tubing.

In addition, radiused edges are provided on the inner edge 76 of the flange portion 68 and at a juncture 84 between the internal surface 40 of the lower end portion 26*a* of the housing and the flange portion 68 to eliminate sharp, high stress points. The flange section 82 also facilitates use of various locking mechanisms for attaching the cannula 18 to the container 12. Such locking mechanisms may include those shown and described in U.S. Pat. No. 5,135,489, incorporated by reference herein.

In assembling the site assembly 14, the septum 24 may be molded of a resilient elastomeric material, such as medical grade rubber, by conventional molding processes such as compression molding. Preferably, the medical grade rubber is West 7389 manufactured by the West Company, Inc. of Lionville, Pa. A lubrication may be applied to the sidewalls 44, and the septum 24 is then inserted downward into an opening 86 defined by the upper end 56 of the housing 26. The septum 24 is pressed downwardly toward the lower end 26*a* of the housing until the septum is inserted into the generally cylindrical internal surface 40. The taper of the upper interior surface 54 facilitates insertion of the septum 24 into the cylindrical lower internal surface 40. Preferably the septum 24 is pressed downward until the septum contacts an upper, generally flat, radially extending surface 88 of the flange 68.

A bonding agent, preferably cyclohexanone, is then applied about the outer surface of the lower end 28*a* of intermediate tube 28. The lower end 28*a* is then inserted into the opening 86 and pushed downward until the land area 64 is in close proximity and preferably contacts the septum 24. The bonding agent then bonds the tube 28 to the housing 26. The housing 26 and attached tubing 28 is then transferred to a slitter device (not shown) for cutting the opening 46 in the septum 24. It is also contemplated that the opening 46 may be cut into the septum at any time, typically after the molding of the septum.

The assembled port assembly 14 may then be subjected to a sterilization process, such as steam, gamma radiation, ethylene oxide or the like and placed in a sterile environment until assembly with the port tube 34 to form the container 12. Separate assembly of the assembly 14 has been found to lower manufacturing costs. The port assembly 14 may be attached to the port tube 34 through the use of a suitable adhesive or the like.

The fabrication of the container 12, including the addition of fluid into the cavity 35, may then be completed. Typically the assembled container 12 is subjected to steam sterilization or other forms of sterilization. As noted previously, the high temperature exposure during the steam sterilization may cause some relaxation of the housing 26; reducing the compression exerted on the septum 24 by the housing. However, proper selection of the materials and thickness of the housing 26 should ensure that the compression exerted on the septum 24 by the housing 26 after steam sterilization is sufficient to sealingly close the opening 46 before and after insertion of the cannula 18.

Referring to FIG. 3, an alternate embodiment of the septum of the present invention is generally indicated at 90. The septum 90 includes an outer circumferential sidewall 92 which is compressed into a generally cylindrical configuration by the housing 26 although preferably the sidewall 92 is formed in a cylindrical shape during fabrication of the septum 90.

The septum 90 is molded to form a lower raised dome portion 94 which is circumscribed by a circumferential flat edge portion 95 which abuttingly contacts the upper surface 88 of the flange 68. The dome portion 94 extends downward through the target area 74 to present an outer convex surface 96. The surface 96 is configured so that a midpoint 96a of the surface extends lower than the inner tapered portion 68b of the radial flange 68.

The upper surface 98 of the septum 90 forms a generally centrally located concave depression 100. The depression 100 is circumscribed by a generally flat, radially extending edge portion 102 which is disposed abuttingly adjacent to the land area 64 of the tube 28. The depression 100 forms a void 104 into which portion of the septum 90 can deform during the insertion of a cannula 18 (FIG. 1) through the opening 46. In addition, the depression 100 is preferably configured so that the thickness of the septum 90 at the opening 106 is generally the same as the thickness of the embodiment of the septum 24 (FIG. 2) at opening 46. Equalizing the thickness of the two septum embodiments gives similar sealing characteristics between the two embodiments.

Referring to FIG. 4 in conjunction with FIG. 1, an additional alternate embodiment of the septum is generally indicated at 110. The septum includes a lower portion 112 and an upper layer 114 which is preferably bonded to an upper surface 116 of the lower portion 112. The upper layer 114 may also be a separate layer located between the lower portion and the container 12. The upper layer 114 provides a barrier between the lower portion 112 and the fluid of the container 12 which may be present in the passageway 29 defined by the tube 28. Preferably the upper layer 114 is formed without any openings and is instead rupturable upon the insertion of the cannula 18 through a resealable opening 118 formed as a slit in the lower portion 112. The opening 118 extends for at least a portion and preferably through the lower portion 12.

Use of the barrier layer 114 prevents contact between the fluid in the container 12 and the lower portion 112 of the septum 110. During storage of the container 12 this barrier may allow the use of resilient materials for the lower portion which may not be suitable for long term contact with the fluid in the cavity 35. Use of the sealing layer 114 thereby may remove the need for placing a sealing membrane (not shown) in the port tube 34 which must be ruptured to allow access to the cavity 35. Therefore the length of the cannula 18 may be reduced since it is no longer necessary to have to extend the tip of the cannula through the septum 110 for a distance sufficient to rupture such a sealing membrane.

Preferably the upper sealing layer 114 is made of TEFLON PTFE and is attached to the lower portion 112 using standard lamination techniques. It is also contemplated that other materials which form non-toxic barriers are also sufficient. However, care must be taken because certain materials may buckle during the radial compression because the materials have compressive moduli which vary from the compressive modulus of the material forming the lower portion 112 of the septum. One method of overcoming this problem is to reduce the percent compression of the septum 110 to the lower end of the range, if the application allows it.

The upper sealing layer 114 may also be bonded to the lower portion 112 after the lower portion 112 is positioned in the housing. One method is to dissolve the material, such as PVC, making up the upper layer 114 in a solvent, placing the mixture on the top surface of the lower portion, and "flashing off" the solvent. Another method is to apply a quantity of molten polymer to the surface of the lower portion 112 whereby the polymer then hardens and bonds to the lower portion.

Septum 110 is compressingly engaged to the housing 26 in a manner which has been described above for the preferred embodiment shown in FIG. 2. In addition, the upper layer 114 being composed of a material different than that of the lower portion 112, provides a surface for the placement of bonding agents to sealingly bond the septum 110 to one or both of the housing 26 and tube 28. This bonding may be accomplished using bonding agents which may not be compatible with the resilient material of the lower portion 112. Bonding the septum 110 to the housing 26 reduces the need for placing the land area 64 of the tube 28 abuttingly adjacent or in close proximity to the septum, although it is preferred that the land area 64 is in abutting contact with the upper layer 114.

Figure 5:
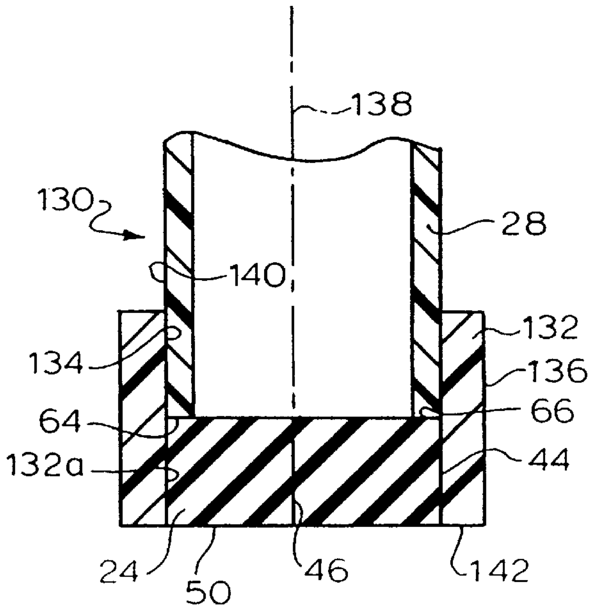
FIG. 5 is an alternate embodiment of a site assembly of the present invention.

Referring to FIG. 5, an alternate embodiment of the site assembly is generally indicated at 130. The site assembly 130 is particularly suited for low cost applications and includes an outer tubular housing 132 having a cylindrical inner surface 134 and a cylindrical outer surface 136. The housing 132 is preferably formed using an extrusion process and is formed so that the inner and outer surfaces 134 and 136 are separated by a constant thickness along the entire length of the housing. The cylindrical inner surface 134 preferably extends with a constant radius about an axis 138. Suitable materials for the housing 132 include polypropylene and other extrudable polymeric materials.

Compressingly disposed within the housing 132 is the septum 24. The septum 24 and housing 132 are sized so that insertion of the septum into the housing sufficiently compresses the septum to seal the opening 46 before insertion and after removal of the cannula 18 (FIG. 1). For example if the site assembly 130 is subjected to steam sterilization, the housing 132 should be of sufficient thickness to maintain the compression on the septum 24 after the sterilization process.

If the housing 132 is not subjected to high temperature sterilization, forming the housing of polypropylene or other suitable extruded material will have little effect on the compression exerted by the housing on the septum 24. Also, even if subjected to high temperature, in several applications the housing 132 made of such a material may relax somewhat but still maintain a compressive force on the septum 24 sufficient to seal the opening 46 before and after insertion of the cannula 18 (FIG. 1) for that particular application.

To prevent the septum 24 from dislodging during removal of the cannula 18 (FIG. 1), the septum is preferably adhesively engaged to one or both of the housing 132 and tube 28. Preferably the adhesive is an ultraviolet cured adhesive and is applied about the sidewalls 44 of the septum 24. Also the lower land area 64 on the tube 28 may abuttingly contact the outer edge portion 66 to support the septum 24 within the housing 132.

The inner surface 134 of the housing is preferably cylindrical to compressingly engage the sidewall 44 and to form the sidewall into a generally cylindrical configuration. It is preferred, however, that the septum 24 is constructed so that the sidewall 44 is generally cylindrical when the septum is in an uncompressed state. The internal surface 134 of the housing 132 is also bonded to the tube 28 by forming a bond between the internal surface of the housing and external surface 140 of the tube 28. A lower end 142 of the housing should be generally flat and flush with the lower surface 50 of the septum.

Figure 6:
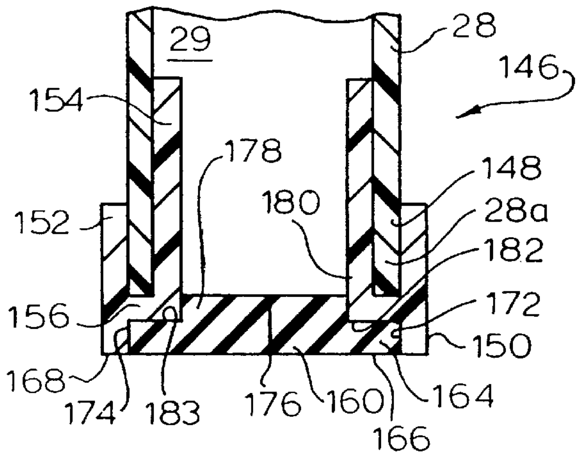
FIG. 6 is a further alternate embodiment of the site assembly.

Referring to FIG. 6, a further alternate embodiment of the site assembly is generally indicated at 146. The site assembly 146 is particularly suited for use in instances where the conduit 28 is relatively thin walled such that a compressive engagement about the exterior of the tubing may cause buckling of the tubing. For example, a port tube 34 is typically formed with thin walls, and so one of the contemplated applications of the site assembly 146 is for use on containers 12 (FIG. 1) which do not have an intermediate tube 30.

In the site assembly 146, the lower end portion 28*a* of the conduit 28 is matingly engaged in an annular slot 148 formed by a housing 150. The housing 150 has an outer annular bracing flange 152 and an inner annular bracing flange 154 which are connected by radial member 156. The outer flange 152 and inner flange 154 form the slot 148 which accepts the lower end 28*a* of the conduit. If the lower end 28*a* of the conduit 28 is cylindrically tubular, the outer and inner flanges 152, 154 are tubular shaped and radial member 156 is configured to form a generally tubular cylindrical slot 148. It is also envisioned that the lower end 28*a* may be of various shapes such as flared outward and the housing 150 configured accordingly to matingly accept such a tube configuration.

The housing 150 is attached to the conduit 28 through adhesive bonding with the adhesives applied to one or both of the surfaces on the inner and outer flanges 152, 154, which contact the conduit 28.

The site assembly 146 also includes a septum 160 which is compressingly disposed in the housing 150. The septum 160 has a lower portion 164 with a lower exposed surface 166 which preferably extends flush with a lower end 168 of the housing 150. An inner, generally cylindrical sidewall surface 172 of the housing 150 adjacent to lower end 168 compressingly engages an outer sidewall 174 of the lower portion 164. The septum 160 and inner sidewall surface 172 are sized so that the septum is compressed sufficiently to seal an opening 176 formed as a slit that extends upwardly though at least a portion, and preferably the entire thickness, of the septum 160. The opening 176 is adapted for allowing the insertion of the cannula 18 (FIG. 1) while sealing about the cannula. The compressive forces exerted on the opening 176 seal the opening before and after removal of the cannula.

The septum 160 may also include an integral upper portion 178 which extends between a generally cylindrical lower end 180 of the inner flange 154. The upper portion 178 and lower end 180 are sized so that the upper portion is sufficiently compressed to reseal the opening 176 which preferably extends through the upper portion.

To support the septum 160 and prevent displacement of the septum into the passageway 29, the inner flange 154 and radial member 156 form a radially extending, flattened land area 182 which supports an outer, generally flat, circumferential edge portion 183 of the lower portion 164 of the septum. To prevent removal of the septum 160 from the site assembly 146, the septum is preferably bonded to the housing 150.

Figure 7:
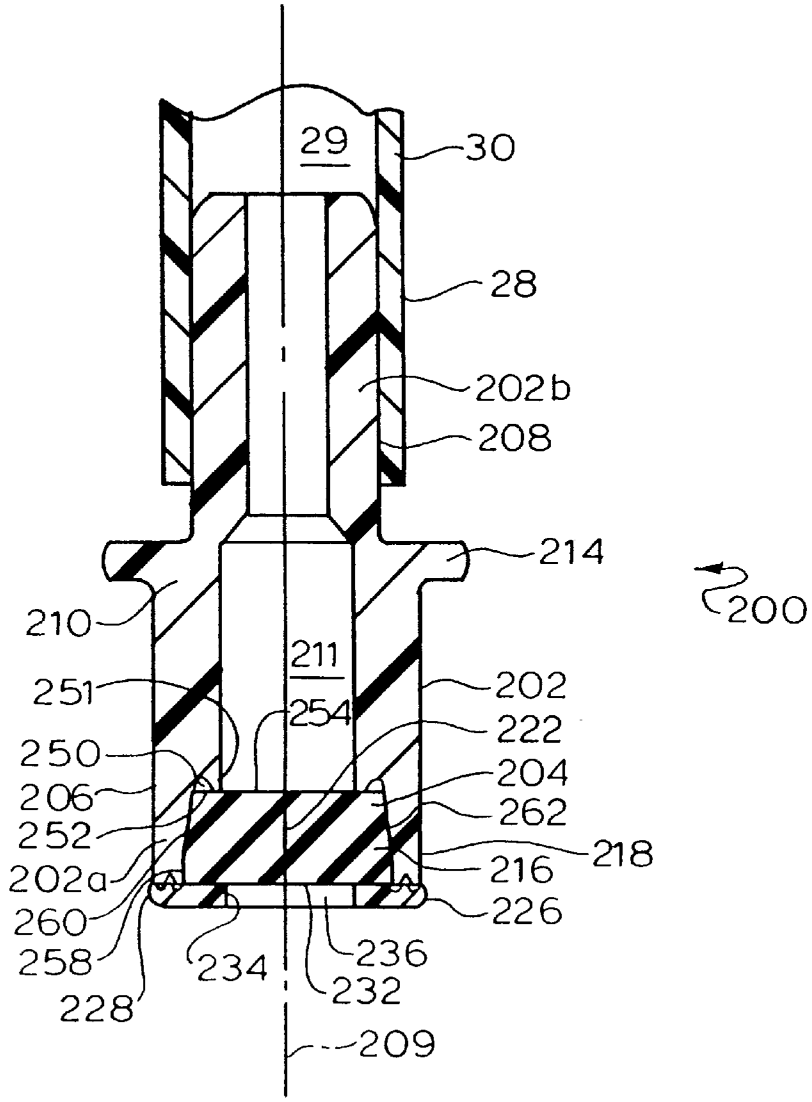
FIG. 7 is a side sectional view of a still further alternate embodiment of the access site of the present invention.
Figure 7A:
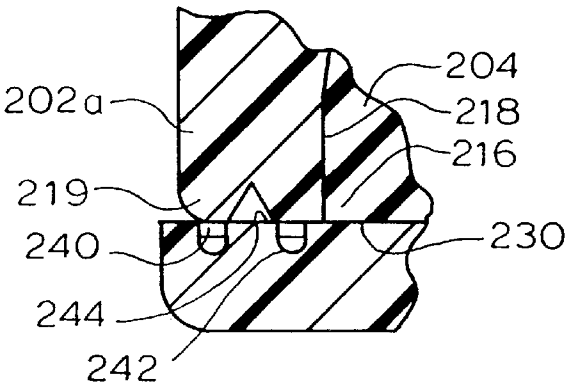
FIG. 7*a* is an enlarged view of a lower portion of the access site of FIG. 7.

Referring to FIGS. 7 and 7*a*, a further alternate embodiment of the resealable site assembly of the present invention is generally indicated at 200. The assembly 200 includes a housing 202 which compressively engages a septum 204 disposed within a lower section 202*a* of the housing. The lower section 202*a* is formed with a tubular configuration having a generally cylindrical external surface 206. Extending upward from and integrally attached to the lower section 202*a* is an upper section 202*b*. The upper section 202*b* is also generally tubular and has a generally cylindrical external surface 208. Both sections 202*a* and 202*b* are concentrically aligned along an axis 209 and form a passageway 211 in fluid communication with the passageway 29 of the conduit 28 such as the intermediate tube 30. The lower section 202*a* is formed with a diameter greater than that of the upper section 202*b*.

The upper section 202*b* is sized to be attached to the conduit 28 preferably by being inserted within the passageway 29. The upper section 202*b* should also be sized so that the external surface 208 contacts the conduit 28 about the circumference of the surface 208 for bonding of the conduit to the housing. The bonding provides sealed attachment of the housing 202 to the conduit 28.

Integrally connected to and extending radially outward from the housing 202, and preferably an upper end 210 of the lower section 202*a*, is a flange 214 which facilitates handling of the assembly 200. The flange 214 also may interlock with locking mechanisms (not shown) for locking the cannula 18 to the site assembly 200. Such locking mechanisms include locking mechanisms shown and described in U.S. Pat. No. 5,135,489 incorporated by reference herein.

A seat 216 is formed within a bottom portion of the lower section 202*a* with the septum 204 compressingly disposed within the seat. Circumferential sidewall 218 extends upward from a lower end 219 of the housing 202 and defines a portion of the seat 216. The sidewall 218, engages the septum 204 and applies an inward radial compressive force on the septum. The compressive force sealingly closes an opening or slit 222 which extends for at least a portion, and preferably entirely through the thickness of the septum 204.

To retain the septum 204 within the seat 216, the assembly 200. includes a ring-shaped flange 226. The flange is connected to the lower end 219 of the housing 202 and has an outer edge 228 generally aligned with the exterior surface 206 of the lower section. The flange 226 extends radially inward over the sidewall 218 and an outer circumferential portion 230 of a lower surface 232 of the septum 204. An inner edge 234 of the flange 226 circumscribes and defines a target area or opening 236 to the septum 204.

Referring in particular to FIG. 7*a*, the lower end 219 of the housing 202 forms at least one and preferably a plurality of downward depending ridges 240. The ridges extend 240 about at least a portion of the circumference of the seat 216 and preferably entirely circumscribe the seat. The ridges 240 are matingly engaged in corresponding channels 242 formed in an upper surface 244 of the flange 214 and are ultrasonically welded within the channels 242 to fixedly attach the flange to the housing 202. Use of sonic welding instead of other methods such as swaging helps to reduce the number of localized stress points.

Referring back to FIG. 7, the lower section 202*a* of the housing 202 is configured to form an annular void 250 and downward depending lip 251 about an outer circumferential portion 252 of an upper surface 254 of the septum 204. The void 250 provides an empty volume into which a portion of the septum 204 may be displaced upon an insertion of the cannula 18 (FIG. 1) into the opening 222, while the lip 251 supports the septum 204.

The seat 216 may be formed so that the sidewall 220 has a lower cylindrical section 258 and an upper tapered section 260 so that a lower end of the seat 216 has a slightly larger diameter than the upper end of the seat. However, the septum 204 is preferably manufactured so that prior to insertion into the seat 216, the septum has generally cylindrical sidewalls 262. Compressively inserting the generally cylindrical septum 204 within the seat 216 having the sidewall 220 with the upper tapered section 260 varies the compression exerted by the housing 202 on the septum over the height of the septum 204. The greater compression being at the upper end portion of the septum. Preferably the compression of the septum 204 at the upper end portion is approximately 11%.

While particular embodiments of the resealable access site for fluid containers have been shown and described, it will be appreciated by those skilled in the art that changes and modifications may be made thereto without departing from the invention in its broader aspects and as set forth in the following claims.

What is claimed is:

1. An access site for allowing a cannula multiple accesses to a fluid passageway, the site comprising;

a first generally flexible conduit having a lower portion defining the passageway, a lower end of the lower portion forming a ring shaped land area;

a housing including a lower portion having an upward extending inner surface, a radially extending flange attached to a lower end of the lower portion and extending inward from the lower portion, the housing also including an upper portion, the lower portion of the first conduit being sealingly attached to the upper portion; and a septum compressingly disposed within the lower portion of the housing, the septum defining an opening extending upward through at least a portion of the septum, the opening sized for sealed insertion of the cannula through the septum, the septum having an upper surface with an upper outer circumferential edge portion and a lower surface with a lower outer circumferential edge portion, the conduit being connected to the housing so that the ring shaped land area is immediately adjacent the upper outer circumferential edge portion of the septum to support the septum against displacement upward upon insertion of the cannula and the radial flange extending over the lower outer circumfernetial edge portion to define a target access opening to the septum.

2. The access site of claim 1 wherein an inner surface of the lower portion of the housing is formed as a cylinder having a constant radius about an axis defined by at least the lower portion of the housing.

3. The access site of claim 1 wherein the upper portion of the housing forms a tapered inner surface.

4. The access site of claim 3 wherein the tapered inner surface extends to the inner surface of the lower portion of the housing.

5. The access site of claim 1 wherein the housing includes a thickened upper end portion.

6. The access site of claim 5 wherein the outer wall of the housing below the thickened upper end portion is cylindrical.

7. The access site of claim 1 wherein the lower radial flange includes a tapered inner edge portion.

8. The access site of claim 1 wherein the land area is in abutting contact with the upper edge portion of the septum.

9. The access site of claim 8 wherein the land area is generally flat and radially extending.

10. The access site of claim 9 wherein the upper edge portion is generally flat and radially extending.

11. The access site of claim 1 wherein the conduit is in fluid communication with a flexible container, the container is formed with a port tube, the port tube being sealingly attached to the conduit.

12. The access site of claim 1 wherein the lower radial flange includes a tapered inner edge portion, the inner edge portion having an inner edge defining the target opening, the septum including a raised dome portion extending downward into the target opening.

13. The access site of claim 12 wherein the upper surface of the septum forms a generally concave shaped void.

14. The access site of claim 1 wherein the septum includes an upper layer and a lower portion attached to the upper layer, the upper layer being composed of a different material than the lower layer.

15. The access site of claim 14 wherein the opening extends only within the lower portion of the septum.

16. The access site of claim 1 wherein the septum is bonded to the housing.

17. The access site of claim 1 further including a barrier layer disposed in close proximity to the septum.

18. The access site of claim 17 wherein the barrier layer forms an upper layer on the septum.

19. The access site of claim 17 wherein the barrier layer is bonded to the septum.

20. The access site of claim 17 wherein the barrier layer is deposited on the upper surface of the septum by flashing off solvent contained within a solution including the solvent and a material forming the barrier layer.

21. The access site of claim 17 wherein the barrier layer is attached to the housing in close proximity to the septum.

* * * * *